United States Patent
Ringemann (10) Patent No.: US 11,998,321 B2
(45) Date of Patent: Jun. 4, 2024

(54) SYSTEM AND A METHOD FOR AUTOMATICALLY MANAGING CONTINUOUS GLUCOSE MONITORING MEASUREMENTS INDICATIVE OF GLUCOSE LEVEL IN A BODILY FLUID

(71) Applicant: Roche Diabetes Care, Inc., Indianapolis, IN (US)

(72) Inventor: Christian Ringemann, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/422,789

(22) Filed: May 24, 2019

(65) Prior Publication Data
US 2019/0274603 A1    Sep. 12, 2019

Related U.S. Application Data (63) Continuation of application No. PCT/EP2017/079777, filed on Nov. 20, 2017.

(30) Foreign Application Priority Data

Nov. 25, 2016 (EP) .................... 16200766

(51) Int. Cl.
*A61B 5/145*   (2006.01)
*A61B 5/00*    (2006.01)
(Continued)

(52) U.S. Cl.
CPC ........ *A61B 5/14532* (2013.01); *A61B 5/0205* (2013.01); *A61B 5/1118* (2013.01);
(Continued)

(58) Field of Classification Search
None
See application file for complete search history.

(56) References Cited

U.S. PATENT DOCUMENTS

2012/0123234 A1    5/2012 Atlas et al.
2013/0267809 A1*   10/2013 Brister ............... A61B 5/14503
                                                       600/347
(Continued)

FOREIGN PATENT DOCUMENTS

CN    102395310 A    3/2012
CN    106021852 A    10/2016
(Continued)

OTHER PUBLICATIONS

Matthaei, Stephan. "Assessing the value of the Ambulatory Glucose Profile in clinical practice." British Journal of Diabetes 14.4 (2014): 148-152.*

(Continued)

*Primary Examiner* — Yi-Shan Yang
*Assistant Examiner* — Samuel C Kim
(74) *Attorney, Agent, or Firm* — Bose McKinney & Evans LLP (57) ABSTRACT

The disclosure relates to a method and system for controlling glucose levels comprising receiving behavioral sensor measurements and analyte sensor measurements, determining a plurality of analyte profiles from continuous analyte sensor measurements; grouping the plurality of analyte profiles into clusters; assigning a selected behavioral parameter or a selected pattern of behavioral parameters to each analyte profile in a first cluster, and providing a treatment recommendation.

18 Claims, 3 Drawing Sheets

(51) Int. Cl.
  *A61B 5/0205*  (2006.01)
  *A61B 5/11*  (2006.01)
  *A61M 5/172*  (2006.01)
  *G16H 20/13*  (2018.01)
  *G16H 20/17*  (2018.01)
  *G16H 20/60*  (2018.01)
  *G16H 40/63*  (2018.01)
  *G16H 50/20*  (2018.01)
  *G16H 50/70*  (2018.01)
  *G16H 10/60*  (2018.01)
  *G16H 50/30*  (2018.01)

(52) U.S. Cl.
  CPC ............ *A61B 5/7264* (2013.01); *A61B 5/742* (2013.01); *A61M 5/1723* (2013.01); *G16H 20/13* (2018.01); *G16H 20/17* (2018.01); *G16H 20/60* (2018.01); *G16H 40/63* (2018.01); *G16H 50/20* (2018.01); *G16H 50/70* (2018.01); *A61B 5/0093* (2013.01); *A61B 5/1112* (2013.01); *A61B 5/14546* (2013.01); *A61B 5/4839* (2013.01); *A61B 5/6801* (2013.01); *A61M 2230/201* (2013.01); *G16H 10/60* (2018.01); *G16H 50/30* (2018.01)

(56) References Cited

U.S. PATENT DOCUMENTS

| | | | | |
|---|---|---|---|---|
| 2014/0046160 | A1* | 2/2014 | Terashima | A61B 5/74 600/365 |
| 2014/0081103 | A1 | 3/2014 | Schaible | |
| 2014/0365136 | A1* | 12/2014 | Mears | G16Z 99/00 702/19 |
| 2016/0098848 | A1* | 4/2016 | Zamanakos | G06T 11/206 345/440 |
| 2016/0328991 | A1* | 11/2016 | Simpson | A61B 5/0022 |
| 2018/0199890 | A1* | 7/2018 | Hayter | A61B 5/7275 |

FOREIGN PATENT DOCUMENTS

| | | | |
|---|---|---|---|
| EP | 2 345 893 A1 | 7/2011 | |
| WO | WO 2004/043230 A2 | 5/2004 | |
| WO | WO 2010/075350 A1 | 7/2010 | |
| WO | WO-2010075350 A1 * | 7/2010 | ......... A61B 5/14532 |
| WO | WO 2012/076148 A1 | 6/2012 | |
| WO | WO 2012/123765 A1 | 9/2012 | |
| WO | WO 2014/116701 A2 | 7/2014 | |

OTHER PUBLICATIONS

International Search Report and Written Opinion, PCT/EP2017/079777, dated Feb. 16, 2018, 18 pages.

International Preliminary Report on Patentability, PCT/EP2017/079777, dated May 28, 2019, 15 pages.

Mazze et al., Ambulatory Glucose Profile: Representation of Verified Self-Monitored Blood Glucose Data, Diabetes Care, 1987, pp. 111-117, vol. 10, issue 1.

Matthaei, Assessing the Value of the Ambulatory Glucose Profile in Clinical Practice, British Journal of Diabetes and Vascular Disease, 2014, pp. 148-152, vol. 14, issue 4.

Bergenstal et al., Recommendations for Standardizing Glucose Reporting and Analysis to Optimize Clinical Decision Making in Diabetes: The Ambulatory Glucose Profile (AGP), Diabetes Tech. & Therapeutics, 2013, pp. 198-211, vol. 15, issue 3.

Anonymous, Ambulatory glucose profile, Wikipedia, Sep. 13, 2016, 4 pages, https://en.wikipedia.org/w/index.php?title=Ambulatory_glucose_profile&oldid=739197287, Retrieved on Feb. 27, 2024.

* cited by examiner

SYSTEM AND A METHOD FOR AUTOMATICALLY MANAGING CONTINUOUS GLUCOSE MONITORING MEASUREMENTS INDICATIVE OF GLUCOSE LEVEL IN A BODILY FLUID

RELATED APPLICATIONS

This application is a continuation of PCT/EP2017/079777, filed Nov. 20, 2017, which claims priority to EP 16 200 766.0, filed Nov. 25, 2016, the entire disclosures of each of which are hereby incorporated herein by reference.

BACKGROUND

The present disclosure refers to a system and a method for automatically analyzing and managing continuous glucose monitoring measurements indicative of glucose level in a bodily fluid.

Glucose monitoring helps people with diabetes manage the disease and avoid its associated problems. A person can use the results of glucose monitoring to make decisions about food, physical activity, and medications. A common way to check glucose levels is performing discontinuous monitoring. Such checking usually involves pricking a fingertip with an automatic lancing device to obtain a blood sample and then using an ex vivo glucose sensor and a glucose meter to measure the blood sample's glucose level. Such monitoring may also be referred to as "spot monitoring."

As an alternative or in addition, continuous glucose monitoring (CGM) may be applied. A system for CGM may use a body sensor inserted under the skin to check glucose levels. The sensor stays in place for several days to weeks and then must be replaced. A transmitter sends information about glucose levels (e.g., via wireless data transmission) from the sensor to a monitor device. The user may check blood samples with a glucose meter to calibrate the devices.

An ambulatory glucose profile (AGP) may be determined (Matthaei, Assessing the Value of the Ambulatory Glucose Profile in Clinical Practice, The British Journal of Diabetes and Vascular Disease; Mazze et al., Ambulatory Glucose Profile Representation of Verified Self-Monitored Glucose Data, 10 Diabetes Care, 111-117 (1987); Bergenstal et al., Recommendations for Standardizing Glucose Reporting and Analysis to Optimize Clinical Decision Making in Diabetes: The Ambulatory Glucose Profile (AGP), 15 Diabetes Tech. & Therapeutics 198-211 (2013)). In a standardized manner, the AGP combines inputs from multiple days of collected CGM data and collates them into a single 24-hour period. AGPs may make glycemic patterns more recognizable.

In the AGP glucose monitoring, presentation data collected over multiple days, e.g., two weeks, are collapsed and plotted according to time (without regard to date) as if they occurred over 24 h, starting and ending at midnight (see, e.g., Bergenstal et al.). Smoothed curves representing the median (50th), 25th and 75th (IQR—inter quartile range), and 10th and 90th frequency percentiles may be depicted in the (24-h) presentation referred to as AGP. At a glance one can observe the time(s) of day when the glucose value is most consistently low or high and when the most variability is occurring (the width of the 25th to 75th percentile (50% of reading) or 10th to 90th frequency (80% of readings)). This is an exercise clinicians can do together with patients in a matter of minutes. For instance, without dependence on numbers, formulas, or derived indices, clinicians and patients can quickly become skilled at identifying the risk of hypoglycemia.

AGP presentation as such, for example, is disclosed in WO 2014/116701 A2.

The document US 2014/0365136 A1 discloses a system and a method for automatically displaying patterns in biological monitoring data. A collection system for automatically displaying patterns in glucose data is provided.

Document WO 2012/123765 A1 discloses a self-monitoring device for attachment to the body, which incorporates real-time and correlated measurement of body movement and physiological analytes of metabolism (e.g., glucose) that can be modulated by physical activity. An object is to provide real time instruction and feedback to the wearer based on current and previous glucose and activity levels to engender immediate action to better maintain glucose control and reduce time spent in hyperglycemia. Beyond basic movement detection by accelerometers attached to the body, a variety of available technologies is described: GPS, heart rate monitoring gyroscopes, wearable fabrics with dynamic properties in response to movement, optical measurement, and cameras.

Document WO 2012/076148 A1 discloses systems and methods for automatically displaying patterns in biological data which may include one or more processors, and machine readable instructions. The machine readable instructions can cause the one or more processors to divide biological data into segments of interest. The one or more processors can transform, automatically, each of the segments of interest into a set of features. The one or more processors can cluster, automatically, the segments of interest into groups of clustered segments. The segments of interest can be grouped in the groups of clustered segments based at least in part upon the set of features. A cluster center can be associated with one of the groups of clustered segments. The one or more processors can present, automatically, the cluster center on a human machine interface.

Document WO 2004/043230 A2 refers to a method of screening for disorders of glucose metabolism such as impaired glucose tolerance and diabetes that allows prevention, or early detection and treatment of diabetic complications such as cardiovascular disease, retinopathy, and other disorders of the major organs and systems. The shape of a subject's glucose profile is evaluated and the profile is classified into one of several predefined clusters, each cluster corresponding either to a normal condition or one of several abnormal conditions. The series of blood glucose values making up the glucose tolerance curve is measured using any glucose analyzer including invasive, minimally invasive or noninvasive types.

Document WO 2010/075350 A1 discloses a method of diabetes analysis. A plurality of glucose level readings for a user is received and analyzed to generate a report which includes a first chart along a 24-hour timeline and a second chart having at least one of infusion device settings and active insulin levels corresponding to the 24-hour timeline of the first chart.

Document EP 2 345 893 A1 discloses a blood-sugar level measurement device with a blood-sugar level sensor and an acceleration sensor for measuring movement information associated with human body activity. A CPU controls whether or not the measurement operation of a blood-sugar measurement circuit can be executed on the basis of the measured movement information. The measured blood-sugar level and movement information are displayed on a display unit. An insulin infusion device, a measurement method, a method for controlling an insulin infusion device and a program are provided.

SUMMARY

The present disclosure provides improved technologies for automatically analyzing continuous glucose monitoring data indicative of glucose level in a bodily fluid.

According to an aspect, a system for automatically analyzing continuous glucose monitoring data indicative of glucose level in a bodily fluid is provided. The system comprises an input device, a data processor, an output device (also referred to as an "output portal"), and machine readable instructions that are executed by the data processor. The machine readable instructions cause the data processor to: receive continuous glucose monitoring data via the input device, the continuous glucose monitoring data indicating a glucose level sampled for a person over time in a continuous glucose level measurement; receive personal behavioral data, the personal behavioral data representing one or more behavioral parameters and, for the one or more behavioral parameters, indicating sensor signals sampled over time for the person by one or more activity sensors; determine a plurality of glucose profiles from the continuous glucose monitoring data; group the plurality of glucose profiles into clusters of one or more glucose profiles according to one or more clustering parameters; assign a selected behavioral parameter or a selected pattern of behavioral parameters from the one or more behavioral parameters to each glucose profile in a first cluster, but not to all or not to any glucose profiles in a second cluster which is different from the first cluster; and provide analysis data to the output device, the analysis data indicating the selected behavioral parameter or the selected pattern of behavioral parameters from the one or more behavioral parameters and the first cluster.

According to another aspect, a method for automatically analyzing continuous glucose monitoring data indicative of a glucose level in a bodily fluid in a system is provided. The system comprises a data processor, an input device, and an output device. The method comprises receiving continuous glucose monitoring data via the input device, the continuous glucose monitoring data indicating a glucose level sampled for a person over time in a continuous glucose level measurement; receiving personal behavioral data, the personal behavioral data representing one or more behavioral parameters and, for the one or more behavioral parameters, indicating sensor signals sampled over time for the person by one or more sensors; determining a plurality of glucose profiles from the continuous glucose monitoring data; grouping the plurality of glucose profiles into clusters of one or more glucose profiles according to one or more clustering parameters; assigning a selected behavioral parameter or a selected pattern of behavioral parameters from the one or more behavioral parameters to each glucose profile in a first cluster, but not to all or not to any glucose profiles in a second cluster which is different from the first cluster; and providing analysis data to the output device, the analysis data indicating the selected behavioral parameter or the selected pattern of behavioral parameters from the one or more behavioral parameters and the first cluster.

Further, a computer program product, preferably stored on a storage medium, is configured to perform the method for analyzing glucose monitoring data indicative of a glucose level during operation on a system for automatically analyzing continuous glucose monitoring data indicative of a glucose level in a bodily fluid, the system comprising a data processor, an input device, and an output device.

Some (sub-group of the plurality of glucose profiles) or each of the plurality of glucose profiles may be assigned one or more of the behavioral parameters.

The order of the steps caused by the machine readable instructions and performed by the processor may be different in various embodiments. For example, measures for clustering of the plurality of glucose profiles may be performed before and/or after the one or more behavioral parameters are assigned.

The continuous glucose monitoring data is a stream of data collected or sampled for person or patient for a plurality of sample times over a measurement time period in a continuous glucose level measurement. The sample time is a parameter that indicates when, during the measurement time period, the respective glucose value is detected in the continuous glucose level measurement. In an embodiment, a glucose profile which may also be referred to as glucose trace comprises a glucose value for each of the plurality of sample times assigned to the glucose profile. The glucose profile comprises a sub-group of the stream of data collected over a sub-measurement time period. Such measurement time period, for example, may, e.g., be 24 hours. In general, the sub-measurement time period will be shorter than the measurement time period.

The selected behavioral parameter or the selected pattern of behavioral parameters that is assigned to each glucose profile in the first cluster distinguishes the glucose profiles in the first cluster from the glucose profiles in the second cluster. The analysis data indicating such a parametric difference provides improved support to the user of the system for understanding a potential link or association between the glucose profiles and the user's activities (behavioral data). The selected behavioral parameter or the selected pattern of behavioral parameters assigned to each glucose profile in the first cluster may not be assigned to any of the glucose profiles in the second cluster. As an alternative, the selected behavioral parameter or the selected pattern of behavioral parameters assigned to each glucose profile in the first cluster may be assigned to less than fifty, or less than twenty, or less than ten percent of the glucose profiles in the second cluster.

The sensor signals indicating the behavioral parameters may be collected by one or more sensor devices.

The machine readable instructions may cause the data processor to cluster the plurality of glucose profiles according to a similarity clustering parameter, the similarity clustering parameter defining a level of similarity between glucose profiles. Glucose profiles may, e.g., be considered similar if more than 70% of the glucose values provided in the glucose profiles to be compared are equal. Two glucose values may be considered equal if a deviation between the two values is less than 20%.

The machine readable instructions may cause the data processor to cluster the plurality of glucose profiles according to a clinical pattern clustering parameter, the clinical pattern clustering parameter defining one or more clinically relevant parameters.

The one or more clinically relevant parameters may be selected from the following group: parameters indicating one of hypoglycemia, nocturnal hypoglycemia, hyperglycemia, post-hypoglycemic hyperglycemia, and glucose variability.

The machine readable instructions may cause the data processor to cluster the plurality of glucose profiles according to a behavioral clustering parameter, wherein the behavioral clustering parameter is defined by at least one of the one or more behavioral parameters.

Personal behavioral data may be selected from the following group: heart rate data, body movement data, breathing rate data, breathing frequency data, GPS data, blood pressure data, and body temperature data. One or more behavioral sensors configured to detect at least one of such personal behavioral parameters may be provided, for example, in an activity tracker which may be carried by the person for which the glucose level is continuously monitored. Such sensors may also be referred to as activity sensor. As an alternative or in addition, sensor signals may be provided in response to receiving a user input. For example, the user may input data characterizing personal behavioral parameters. In this embodiment, as understood according to the present disclosure, the input device receiving the user input data is acting as a behavioral sensor. As an alternative or in addition, sensor signals may be provided in response to receiving a device input. For example, the sensor signals indicated by the personal behavioral data may be received from some device configured to detect personal behavioral data. In an embodiment, the signals are received from an insulin pump, the signals indicating, for example, an insulin medication. With regard to insulin medication by the pump or manually, different characteristics may be indicated by the signals, e.g., time of insulin medication and/or amount of insulin bolus.

The machine readable instructions may cause the data processor to determine an ambulatory glucose profile (AGP) for the one or more glucose profiles from at least one of the first and second cluster. In one embodiment, AGPs are determined for the first and second clusters, and optionally juxtaposed.

The machine readable instructions may further cause the data processor to assign to some or each of the glucose profiles one of the one or more behavioral parameters and determine that a selected behavioral parameter or a selected pattern of behavioral parameters from the one or more behavioral parameters is assigned to each glucose profile in a first cluster, but not to all or not to any glucose profiles in a second cluster which is different from the first cluster.

The machine readable instructions may cause the data processor to provide a recommendation to the user through the output device.

The machine readable instructions may cause the data processor to provide a recommendation that is derived from an analysis of the result of assigning behavioral parameters to some or each glucose profile in the first cluster and/or the second cluster and/or from an analysis of an ambulatory glucose profile for the one or more glucose profiles from at least one of the first and second cluster. The recommendation may be derived from an analysis of the result of assigning behavioral parameters to some or each glucose profile in the first cluster and/or the second cluster. In addition or as an alternative, the AGPs determined for the clusters may be analyzed to derive a recommendation for the user/patient. For example, the output provided by the output device may recommend taking food and/or applying an insulin bolus. The recommendation may indicate an insulin bolus and/or a time for an action recommended to the user/patient.

With regard to glucose measurement or monitoring, a glucose level or value may be determined by continuous glucose monitoring (CGM) via a fully or partially implanted sensor. In general, in the context of CGM, a glucose value or level in a bodily fluid may be determined. The analyte value may be, e.g., subcutaneously measured in an interstitial fluid. CGM may be implemented as a nearly real-time monitoring procedure frequently or automatically providing/updating analyte values without user interaction.

The alternative embodiments described above with regard to the system may also apply to the method for automatically analyzing continuous glucose monitoring data indicative of a glucose level.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
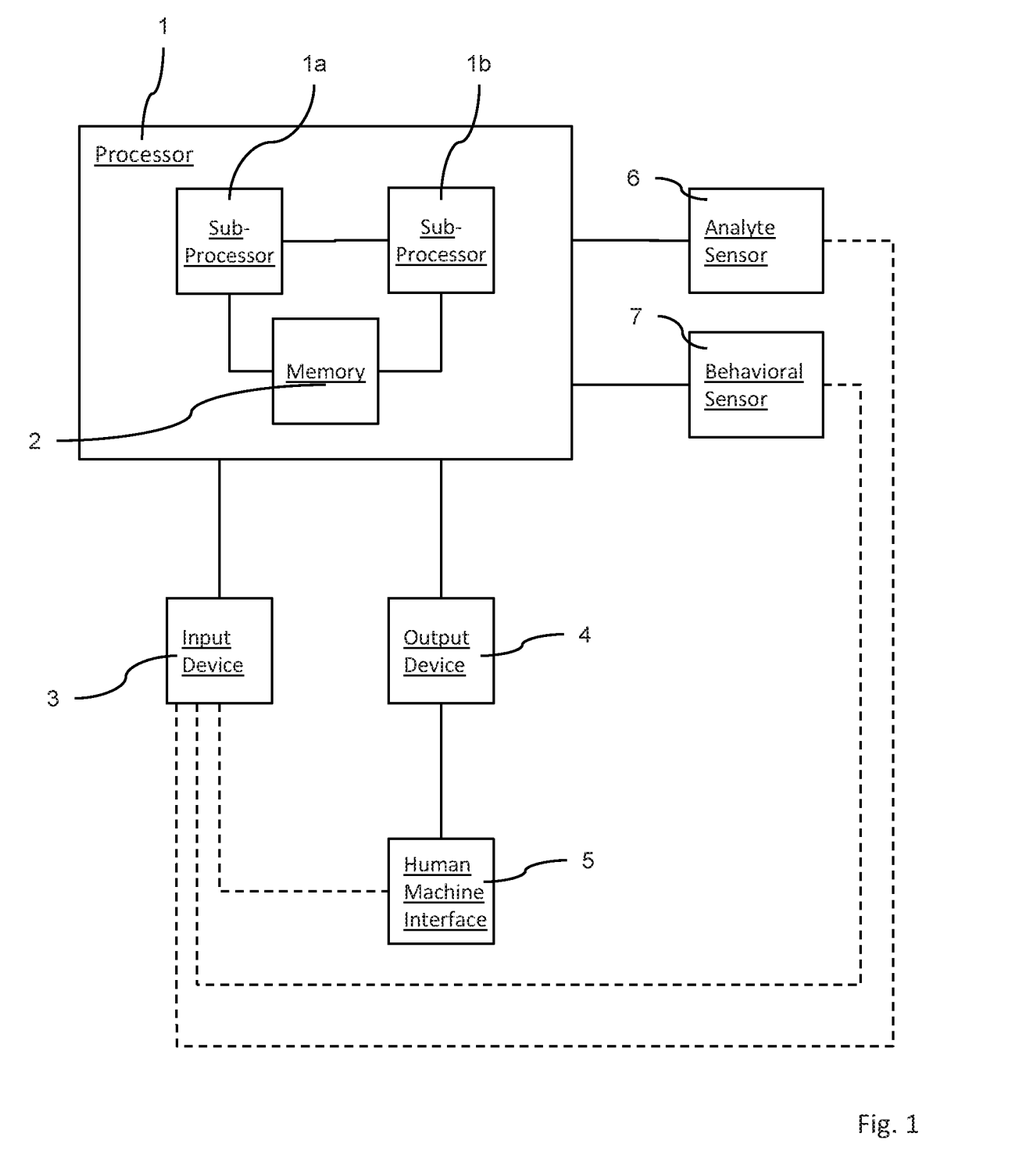
FIG. 1 shows a schematic representation of a system for automatically analyzing and displaying continuous glucose monitoring data indicative of a glucose level.

FIG. 1 generally depicts an embodiment of a system for automatically analyzing and displaying continuous glucose monitoring data indicative of a glucose level in a bodily fluid. In an embodiment, the system may be configured to automatically analyze and display continuous blood glucose monitoring data indicative of a blood glucose level. The system generally comprises a processor 1 provided with one or more sub-processors 1a, 1b. Also, the processor 1 comprises a memory 2 for storing machine readable instructions. The processor 1 is connected to an input device 3 configured to receive electronic data and an output device 4 configured for outputting electronic data. The input device 3 and the output device 4 may be implemented integrally with processor 1.

A human machine interface 5 is communicably coupled to the output device 4 and, optionally or alternatively, to the input device 3.

Machine readable instructions are provided which are executed by the processor 1 for automatically analyzing continuous glucose monitoring data indicative of a glucose level. Various embodiments of the system and methods for automatically analyzing continuous glucose monitoring data indicative of a glucose level will be described in more detail herein.

The one or more sub-processors 1a, 1b may be a controller, an integrated circuit, a microchip, a computer, or any other computing device capable of executing machine readable instructions. The memory 2 may be RAM, ROM, a flash memory, a hard drive, or any device capable of storing machine readable instructions.

In the embodiments described herein, the one or more sub-processors 1a, 1b may be integral with a single component of the system. However, it is noted that the one or more sub-processors 1a, 1b may be separately located within discrete components such as, for example, a glucose meter, a medication delivery device, a mobile phone, a portable digital assistant (PDA), a mobile computing device such as a laptop, a tablet, or a smart phone, a desktop computer, or a server, e.g., via cloud or web based technologies, and the sub-processors 1a, 1b may be communicatively coupled with one another. It is to be appreciated that in at least one embodiment of the mobile computing device which is useful with one or more embodiments disclosed herein, such a device may include a touch screen and the computing ability to run computational algorithms and/or processes, such as those disclosed herein, and applications, such as an electronic mail program, a calendar program for providing a calendar, as well as provide cellular, wireless, and/or wired connectivity and one or more of the functions of a glucose meter, a digital media player, a digital camera, a video camera, a GPS navigation unit, and a web browser that can access and properly display web pages. Accordingly, the system may include a plurality of components each having one or more sub-processors 1a, 1b that are communicatively coupled with one or more of the other components. Thus, the systems may utilize a distributed computing arrangement to perform any of the machine readable instructions described herein.

The system further comprises the human machine interface 5 communicatively coupled to the processor 1 for receiving signals from the output device 4 and presenting graphical, textual and/or auditory information. The human machine interface 5 may include an electronic display such as, for example, a liquid crystal display, thin film transistor display, light emitting diode display, a touch screen, or any other device capable of transforming signals from a processor into an optical output, or a mechanical output, such as, for example, a speaker, a printer for displaying information on media, and the like.

Embodiments of the present disclosure also comprise machine readable instructions that includes logic or an algorithm written in a programming language such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as implemented via either a field-programmable gate array (FPGA) configuration or an application-specific integrated circuit (ASIC), and their equivalents. Accordingly, the machine readable instructions may be implemented in any conventional computer programming language, as pre-programmed hardware elements, or as a combination of hardware and software components. Moreover, machine readable instructions can be distributed over various components that are communicatively coupled such as, for example, via wires, via a wide area network, via a local area network, via a personal area network, and the like. Thus, any components of the system can transmit signal over the Internet or World Wide Web.

Referring still to FIG. 1, the system may optionally include a body sensor (also referred to as an "analyte sensor") 6 communicatively coupled to the processor 1 for providing biological data indicative of properties of an analyte. In one embodiment, the body sensor 6 is a glucose sensor configured to detect glucose levels (e.g., glucose concentrations) when placed just under the skin of a patient. For example, the body sensor 6 can be a disposable glucose sensor that is worn under the skin for a few days until replacement is needed. As is noted above, the body sensor 6 can be communicatively coupled with the processor, which can be located within various discrete components. Accordingly, in the case of a glucose sensor, the body sensor 6 can be communicatively coupled with, for example, a smart glucose meter, or a medication delivery device and can provide CGM data, i.e., glucose data that is sampled continuously throughout the lifetime of the sensor. The system may also include behavioral sensors 7, discussed below.

According to the embodiments described herein, the one or more sub-processors 1a, 1b of the processor 1 can execute machine readable instructions to automatically analyze continuous glucose monitoring data indicative of a glucose level.

Figure 2:
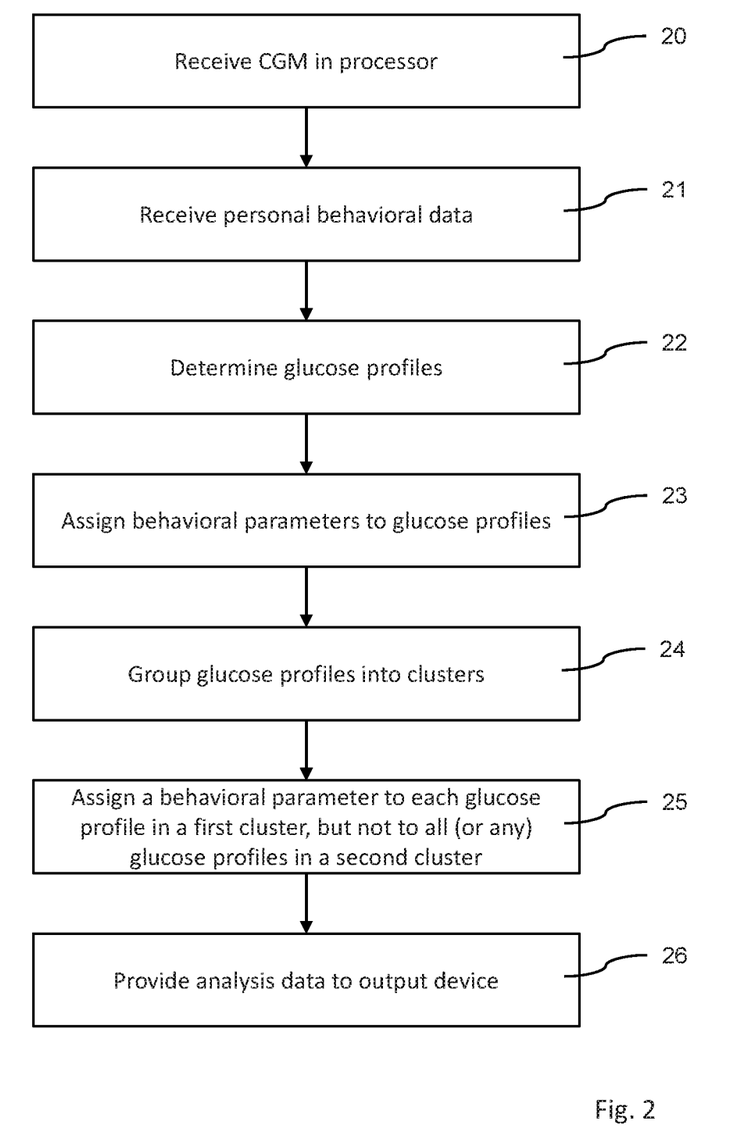
FIG. 2 is a schematic block diagram of a method for operating the system for automatically analyzing and displaying continuous glucose monitoring data indicative of a glucose level.

Referring to FIG. 2, a method for automatically analyzing continuous glucose monitoring data indicative of a glucose level is described. In step 20, continuous glucose monitoring data (measurements) are received in the data processor 1 via the input device 3, or, in an alternative embodiment, directly from the body sensor 6. The continuous glucose monitoring data are indicating a glucose level detected for a person over time in a continuous glucose level measurement. By the measurement so-called CGM measurements (CGM—Continuous Glucose Monitoring) are provided.

Personal behavioral data, e.g., sensor measurements, are received by the processor 1 in step 21. The personal behavioral data represent or are associated with one or more behavioral parameters for the person. The personal behavioral data are sensor signals sampled for the one or more behavioral parameters over time for the person by one or more behavioral sensors 7. Such sampling, at least in part, may overlap in time with the CGM data detection. The one or more sensors may be configured to detect one or more personal behavioral parameters. The personal behavioral data may be selected from the following group: heart rate, body movement, breathing rate, breathing frequency, GPS data (GPS—Global Positioning System), blood pressure data, and body temperature data. One of skill in the art would recognize that the term "behavioral measurement," as used in accordance with this disclosure, encompasses, e.g., heart rate, respiration, location, acceleration, user input, etc. Similarly, the term "behavioral sensor" shall be broadly construed in accordance with this disclosure as covering a wide variety of sensing devices, such as a GPS monitor, breathing rate monitor, breathing frequency monitor, body movement monitor, heartrate monitor, and further extends to sensors that directly measure behavioral parameters, such as activity trackers (e.g., the activity tracker sold under the trademark FITBIT®) or medication delivery devices, as well as devices for manual entry of behavioral parameters, etc.

In step 22, the continuous glucose monitoring data is divided into a plurality of glucose profiles. Various methods for separating continuous glucose monitoring data into glucose profiles are known.

Following, in step 23, at least one of the one or more behavioral parameters is assigned to some or each of the plurality of glucose profiles. The glucose profiles are linked to one or more of the personal behavioral parameters by the assignment. For example, a glucose profile may correspond in time to an activity such as physical exercise like jogging or walking. Therefore, activity parameter(s) indicating such jogging or walking, for example at least one of heart rate, breathing rate, and GPS data, are assigned to the respective glucose profile.

In step 24, the plurality of glucose profiles are grouped into clusters of one or more glucose profiles according to one or more clustering parameters. For example, the grouping may be done based on the personal behavioral parameters. All glucose profiles to which a certain GPS data parameter is assigned may be grouped into one cluster. As an alternative, the plurality of glucose profiles may be grouped according to a clinical pattern clustering parameter, the clinical pattern clustering parameter defining one or more clinically relevant parameters. The one or more clinically relevant parameters may be selected from the following group: parameters indicating one of hypoglycemia, nocturnal hypoglycemia, hyperglycemia, post-hypoglycemic hyperglycemia, and glucose variability.

Further, in an alternative embodiment, the plurality of glucose profiles may be grouped according to the level of similarity between the glucose profiles. If a number of glucose profiles are determined to be similar enough to satisfy one or more "similarity clustering parameters," such glucose profiles may be grouped in a single cluster.

With regard to some of the above embodiments, the assignment of the at least one of the one or more behavioral parameters to some or all of the plurality of glucose profiles may be done prior to the clustering of the plurality of glucose profiles. For example, behavioral parameters would be assigned to the glucose profiles before clustering the profiles according to a personal behavioral parameter. In an alternative embodiment, the clustering is done before the assignment of the at least one behavioral parameter. For example, behavioral parameters could be assigned after clustering the glucose profiles according to a clinically relevant parameter.

In step 25 it is determined or concluded that a selected behavioral parameter or a selected pattern of behavioral parameters from the one or more behavioral parameters is assigned to each glucose profile in a first cluster, but not to all or not to any glucose profile in a second cluster which is different from the first cluster. By analyzing details of the assignment of the selected behavioral parameter or the selected pattern of behavioral parameters to the glucose profiles, the first and the second clusters may be identified. Thereby, conclusions may be made as to some link between the first cluster of glucose profiles and the one or more selected behavioral parameters.

Finally, according to FIG. 2, in step 26 analysis data are provided to the output device 4. The analysis data indicate the selected behavioral parameter or the selected pattern of behavioral parameters and the first cluster of glucose profiles. Based on the analysis data a graphical representation representing the analysis data may be provided on the human machine interface 5, which, for example, is provided with a display.

Optionally, for each cluster of glucose profiles an ambulatory glucose profile (AGP) may be determined as known as such. Signal data may be generated and output through the display, for example, by presenting a graphical representation of the AGPs.

Figure 3:
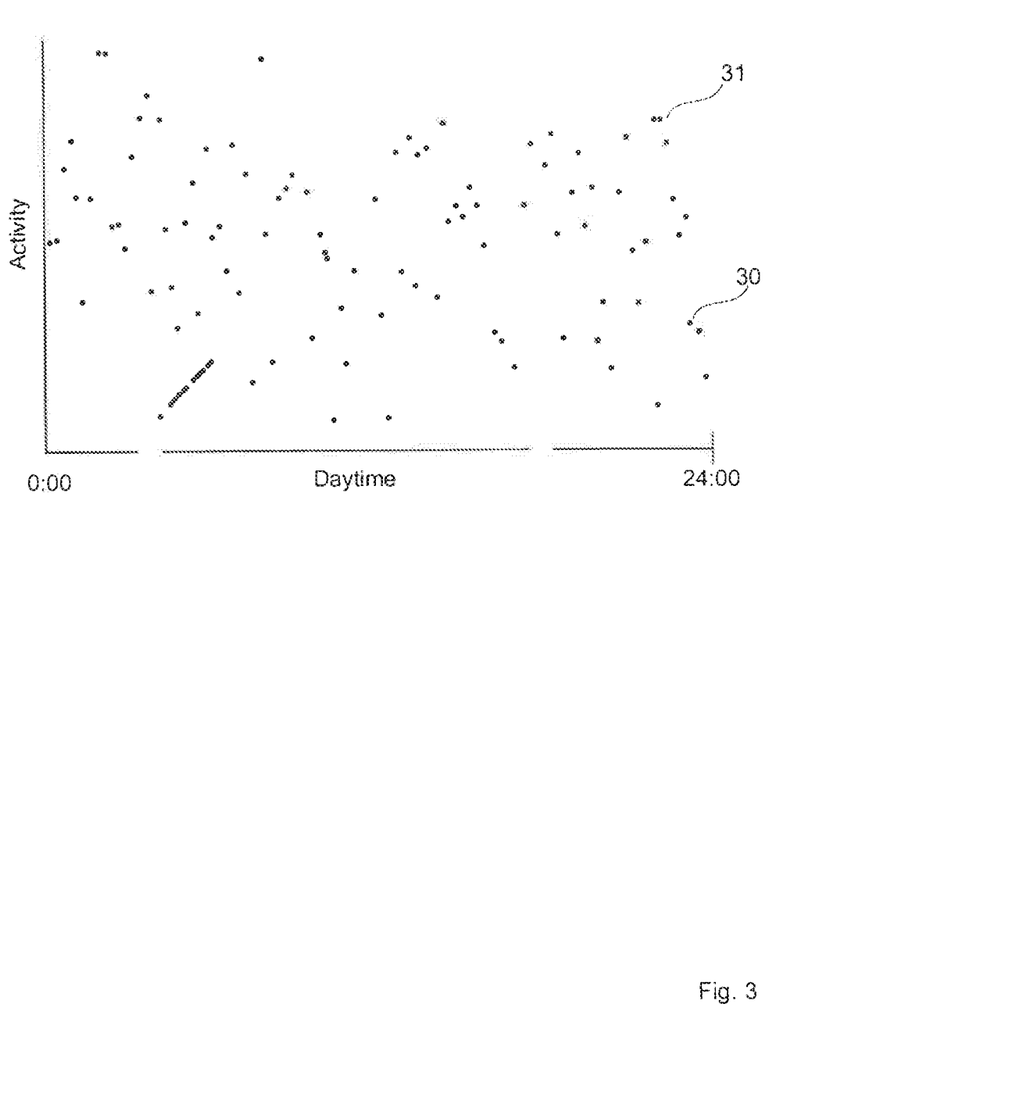
FIG. 3 illustrates a graphical representation of data points for an activity parameter over day time, each of the data points representing a glucose profile.

FIG. 3 refers to an embodiment of the graphical representation depicting glucose profiles. In FIG. 3 data points 30 represent, for example, 24 h continuous glucose monitoring data to which it is assigned a specific clinically relevant pattern as a clustering parameter. For such analysis, for example, a support vector machine (SVM) may be applied. SVM, being a tool for classification of objects known as such, may also be applied in other cases as an algorithm for classification. Further data points 31 represent 24$h$ continuous glucose monitoring data without such specific clinically relevant pattern. From the graphical representation in FIG. 3 it is concluded that the 24 h continuous glucose monitoring data linked to the specific clinically relevant pattern is associated with the behavioral parameter "low activity in the evening hours".

For each of the 24 h continuous glucose monitoring data represented by the data points 30 and the further data points 31 (each providing a cluster), respectively, an AGP may be determined. With regard to the two AGPs, a parameter "low activity" (in the evening) is assigned to one of the two AGPs (regarding data points 30), but not to the other AGP, i.e., the AGPs are differentiated according to activity at a certain time of day.

In general, with regard to the combined analysis of the continuous glucose monitoring data and the personal behavioral data, different embodiments may be pursued. In an embodiment, the glucose profiles are initially clustered according to a self-similarity with a specific cluster algorithm. Following, it is determined whether one or more behavioral parameters (from the information of the non-glucose sensors) assigned to the glucose profiles clustered using self-similarity are typical for such glucose profiles with self-similarity. The one or more behavioral parameters assigned to the glucose profiles for which self-similarity was determined are not assigned to glucose profiles for which self-similarity is not found, such glucose profiles with no self-similarity may be provided in one or more other clusters.

In an alternative embodiment, the glucose profiles are sorted or clustered according to predefined clinically relevant patterns, e.g., too high glucose values after sport, or too low glucose values for more than 5 minutes. Following, it is determined whether one or more behavioral parameters or patterns (from the information of the sensors not used for the initial sorting) assigned to the glucose profiles of one or more clusters each defined by one or more predefined clinically relevant patterns are typical of those clusters. The one or more behavioral parameters assigned to the glucose profiles in the one or more clusters are not assigned to other glucose profiles to which the one or more predefined clinically relevant patterns do not apply. The clinically relevant patterns may be already predefined or can be compiled online by the physician.

In another alternative embodiment, clustering parameters representing one or more behavioral parameter, which may be received from third party equipment (e.g., an activity tracker like the one sold under the trademark FITBIT®), are used for clustering the glucose profiles in different groups. Based on such analysis, for the profiles of the clusters, AGPs are created for the different groups (clusters). The AGPs can then be compared to identify the influence of behavioral parameter patterns which are reflected by the data of the third party equipment.

Regardless of the approach used, AGPs may be obtained which are sorted according to a selected behavioral parameter or a selected pattern of behavioral parameter.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method of managing glucose levels in a body fluid, comprising:

a) receiving continuous glucose measurements from a glucose sensor;
b) receiving behavioral measurements from one or more behavioral sensors and associating the behavioral measurements with one or more behavioral parameters;
c) dividing the continuous glucose measurements into a plurality of glucose profiles wherein each of the plurality of glucose profiles covers a different time interval;
d) grouping the plurality of glucose profiles into at least a first cluster and a second cluster different from the first cluster using a clustering parameter that comprises a clinically relevant parameter wherein the clinically relevant parameter is selected from the following group: parameters indicating one of hypoglycemia, nocturnal hypoglycemia, hyperglycemia, post-hypoglycemic hyperglycemia, and glucose variability;
e) assigning a selected one of the one or more behavioral parameters to a first subset of the plurality of glucose profiles but not to all of the plurality of glucose profiles and wherein each glucose profile in the first cluster is a member of the first subset, but less than all of the glucose profiles in the second cluster is a member of the first subset;
f) presenting the selected one of the one or more behavioral parameters and the first cluster; and
g) generating a treatment recommendation based upon an analysis of the results of step f) to prevent hyperglycemia wherein the treatment recommendation is an insulin bolus and administering the insulin bolus.

2. The method according to claim 1, further comprising creating an ambulatory glucose profile for one of the first cluster and the second cluster; and
wherein the treatment recommendation and a recommended time for administering the treatment recommendation is derived from an analysis of the ambulatory glucose profile.

3. The method according to claim 1, wherein the assigning of the selected one of the one or more behavioral parameters of step e) is performed before step d).

4. The method according to claim 1, wherein:
the grouping in step d) comprises using a clustering parameter that comprises at least one of the one or more behavioral parameters; and
wherein the assigning of the selected one of the one or more behavioral parameters of step e) is performed before step d).

5. The method according to claim 1, wherein the one or more behavioral sensors measure at least one of the following: heart rate data, body movement data, breathing rate data, breathing frequency data, GPS data, blood pressure data, and body temperature data.

6. The method according to claim 1, further comprising creating an ambulatory glucose profile for at least one of the first cluster and the second cluster.

7. The method according to claim 1, wherein step e) further comprises providing on a display the selected behavioral parameter and the first cluster.

8. The method of claim 1, further comprising determining a first ambulatory glucose profile for the first cluster and a second ambulatory glucose profile for the second cluster and displaying the first and second ambulatory glucose profiles in a juxtaposed arrangement.

9. The method of claim 1, wherein plurality of glucose profiles are grouped into a plurality of clusters that includes the first and second clusters and wherein each cluster of the plurality of clusters are classified according by an activity level occurring at a particular time of day.

10. The method according to claim 1, wherein step e) is performed for a plurality of behavioral parameters and the selected one of the one or more behavioral parameters of step f) is a selected pattern of at least two behavioral parameters.

11. A method of managing glucose levels in a body fluid, comprising:
a) receiving continuous glucose measurements from a glucose sensor;
b) receiving behavioral measurements from one or more behavioral sensors and associating the behavioral measurements with one or more behavioral parameters;
c) dividing the continuous glucose measurements into a plurality of glucose profiles wherein each of the plurality of glucose profiles covers a different time interval;
d) grouping the plurality of glucose profiles into at least a first cluster and a second cluster different from the first cluster using a clustering parameter that comprises a clinically relevant parameter wherein the clinically relevant parameter is selected from the following group: parameters indicating one of hypoglycemia, nocturnal hypoglycemia, hyperglycemia, post-hypoglycemic hyperglycemia, and glucose variability;
e) assigning a selected one of the one or more behavioral parameters to a first subset of the plurality of glucose profiles but not to all of the plurality of glucose profiles and wherein each glucose profile in the first cluster is a member of the first subset, but less than all of the glucose profiles in the second cluster is a member of the first subset;
f) presenting the selected one of the one or more behavioral parameters and the first cluster; and
g) generating a treatment recommendation based upon an analysis of the results of step f) to prevent hypoglycemia wherein the treatment recommendation is an ingestion of food and administering the ingestion of food.

12. A method of managing glucose levels in a body fluid, comprising:
a) receiving continuous glucose measurements from a glucose sensor;
b) receiving behavioral measurements from one or more behavioral sensors and associating the behavioral measurements with one or more behavioral parameters;
c) dividing the continuous glucose measurements into a plurality of glucose profiles wherein each of the plurality of glucose profiles covers a different time interval;
d) grouping the plurality of glucose profiles into at least a first cluster and a second cluster different from the first cluster using a clustering parameter that comprises a level of similarity between the glucose profiles;
e) assigning a selected one of the one or more behavioral parameters to a first subset of the plurality of glucose profiles but not to all of the plurality of glucose profiles and wherein each glucose profile in the first cluster is a member of the first subset, but less than all of the glucose profiles in the second cluster is a member of the first subset;
f) presenting the selected one of the one or more behavioral parameters and the first cluster; and
g) creating an ambulatory glucose profile for at least one of the first cluster and the second cluster and generating a treatment option wherein the treatment option is determined based upon an analysis of the ambulatory glucose profile to prevent hyperglycemia wherein the treatment option is an insulin bolus and administering the insulin bolus.

13. The method according to claim 12, wherein the assigning of the selected one of the one or more behavioral parameters of step e) is performed before step d).

14. The method according to claim 12, wherein the treatment option further comprises a recommended time for administering the treatment option and the step of administering the insulin bolus occurs at the recommended time.

15. The method according to claim 5, wherein step e) is performed for a plurality of behavioral parameters and the selected one of the one or more behavioral parameters of step f) is a selected pattern of at least two behavioral parameters.

16. A method of managing glucose levels in a body fluid, comprising:
   a) receiving continuous glucose measurements from a glucose sensor;
   b) receiving behavioral measurements from one or more behavioral sensors and associating the behavioral measurements with one or more behavioral parameters;
   c) dividing the continuous glucose measurements into a plurality of glucose profiles wherein each of the plurality of glucose profiles covers a different time interval;
   d) grouping the plurality of glucose profiles into at least a first cluster and a second cluster different from the first cluster using a clustering parameter that comprises a level of similarity between the glucose profiles;
   e) assigning a selected one of the one or more behavioral parameters to a first subset of the plurality of glucose profiles but not to all of the plurality of glucose profiles and wherein each glucose profile in the first cluster is a member of the first subset, but less than all of the glucose profiles in the second cluster is a member of the first subset;
   f) presenting the selected one of the one or more behavioral parameters and the first cluster; and
   g) creating an ambulatory glucose profile for at least one of the first cluster and the second cluster and generating a treatment option wherein the treatment option is determined based upon an analysis of the ambulatory glucose profile to prevent hypoglycemia wherein the treatment option is the consumption of food and administering the consumption of food.

17. A glucose management system, comprising:
a medication delivery device; and
a processor configured to:
   a) receive continuous glucose measurements measured with a glucose sensor;
   b) receive behavioral measurements measured with one or more behavioral sensors, and associate the behavioral measurements with one or more behavioral parameters;
   c) divide the continuous glucose measurements into a plurality of glucose profiles wherein each of the plurality of glucose profiles covers a different time interval;
   d) group the plurality of glucose profiles into at least a first cluster and a second cluster different from the first cluster using i) a clustering parameter that comprises a level of similarity between the glucose profiles and/or ii) a clustering parameter that comprises a clinically relevant parameter wherein the clinically relevant parameter is selected from the following group: parameters indicating one of hypoglycemia, nocturnal hypoglycemia, hyperglycemia, post-hypoglycemic hyperglycemia, and glucose variability;
   e) assign a selected one of the one or more behavioral parameters to each glucose profile in the first cluster, but less than all of the glucose profiles in the second cluster;
   f) present the selected one of the one or more behavioral parameters and the first cluster; and
   g) generate a treatment option and a recommended time for administering the treatment option wherein the treatment option and the recommended time are determined based upon an analysis of an ambulatory glucose profile determined for the first cluster and wherein the treatment option is an insulin bolus and the glucose management system is further configured to automatically administer the insulin bolus with the medication delivery device at the recommended time.

18. The glucose management system according to claim 17, further comprising a display configured to display the selected behavioral parameter and the first cluster.

* * * * *

UNITED STATES PATENT AND TRADEMARK OFFICE
CERTIFICATE OF CORRECTION

PATENT NO. : 11,998,321 B2
APPLICATION NO. : 16/422789
DATED : June 4, 2024
INVENTOR(S) : Christian Ringemann It is certified that error appears in the above-identified patent and that said Letters Patent is hereby corrected as shown below:

In the Claims

Column 13, Line 11, Claim 15, "claim 5" should be --claim 12--.

Signed and Sealed this
Sixteenth Day of July, 2024

Katherine Kelly Vidal
Director of the United States Patent and Trademark Office